(12) United States Patent
Kennedy

(10) Patent No.: US 8,603,640 B2
(45) Date of Patent: Dec. 10, 2013

(54) HYDROFLUOROALKANES AS CARRIER SOLVENTS FOR TIMBER PRESERVATION

(76) Inventor: Michael Kennedy, Indooroopilly (AU)

( * ) Notice: Subject to any disclaimer, the term of this patent is extended or adjusted under 35 U.S.C. 154(b) by 0 days.

(21) Appl. No.: 13/255,814

(22) PCT Filed: Mar. 12, 2010

(86) PCT No.: PCT/AU2010/000278
§ 371 (c)(1),
(2), (4) Date: Sep. 9, 2011

(87) PCT Pub. No.: WO2010/102338
PCT Pub. Date: Sep. 16, 2010

(65) Prior Publication Data
US 2012/0003492 A1    Jan. 5, 2012

(30) Foreign Application Priority Data
Mar. 13, 2009    (AU) ................. 2009901078

(51) Int. Cl.
*B32B 21/04*    (2006.01)

(52) U.S. Cl.
USPC ............... 428/537.1; 428/536; 117/102 R; 427/297; 106/17

(58) Field of Classification Search
USPC ........ 428/537.1; 117/102 R; 427/297; 106/17
See application file for complete search history.

(56) References Cited

U.S. PATENT DOCUMENTS

| | | | |
|---|---|---|---|
| 3,874,908 A * | 4/1975 | Liddell | 427/345 |
| 4,051,282 A | 9/1977 | Davies | |
| 4,075,121 A * | 2/1978 | Konno et al. | 252/407 |
| 4,143,010 A | 3/1979 | Rak | |
| 4,668,539 A * | 5/1987 | Leonard et al. | 427/298 |
| 4,786,326 A * | 11/1988 | Grove | 106/15.05 |
| 6,235,404 B1 * | 5/2001 | Frater | 428/607 |

FOREIGN PATENT DOCUMENTS

| | | | |
|---|---|---|---|
| GB | 1377061 A | | 12/1974 |
| GB | 2137242 A | | 10/1984 |
| WO | WO02006/092673 | * | 9/2006 |
| WO | WO-2006/092673 A1 | | 9/2006 |

OTHER PUBLICATIONS

European Supplementary Search Report dated May 6, 2013.

* cited by examiner

*Primary Examiner* — Leszek Kiliman
(74) *Attorney, Agent, or Firm* — Edwards Wildman Palmer LLP; Jeffrey D. Hsi

(57) ABSTRACT

A non-supercritical method for impregnating a refractive timber substrate with an active agent, including preparing an impregnation fluid including a low boiling solvent (methane, ethane, propane, butane, isobutane, fluorinated hydrocarbons such as chlorodifluoromethane (R22), 1,1,1,2-tetrafluoroethane (R134a), 1,1,1-trifluoroethane (R143a), pentafluoroethane (R125), 1,1-difluoroethane (R152a) and difluoromethane (R32) and an active agent; contacting a refractive timber substrate (eg heartwood of radiata pine, spruce species; Douglas fir, fir, poplar, willow, sapwood of cypress pine and certain eucalypt and pine species such as heartwood of messmate, larch, western red cedar, European oak and American white oak) with said impregnation fluid in a liquid state in an impregnation chamber for a time sufficient to allow said fluid to penetrate the pores of said refractive timber substrate; and removing said impregnation fluid in a liquid state from said impregnation chamber and returning to a reservoir.

29 Claims, 1 Drawing Sheet

HYDROFLUOROALKANES AS CARRIER SOLVENTS FOR TIMBER PRESERVATION

CROSS-REFERENCE TO RELATED APPLICATIONS

This application is the U.S. National Phase Application of PCT/AU2010/000278, which, claims the benefit of the following Australian Application No.: 2009901078, filed on Mar. 13, 2009; the entire contents of each of these applications is hereby incorporated by reference.

FIELD OF THE INVENTION

The invention relates to non-supercritical methods for impregnating refractory substrates. The invention will be described with reference to the impregnation of refractory timbers with agents which counter degradation thereof, but it will be appreciated that the invention is not limited to those uses.

BACKGROUND ART

Any discussion of the prior art throughout the specification should in no way be considered as an admission that such prior art is widely known or forms part of common general knowledge in the field.

The simplest procedure for incorporating an active agent into a porous material, such as wood, is to soak the porous material in a bath containing a solution in which is dissolved or suspended an active agent, allowing the solution to penetrate into the pores of the porous material, removing the soaked material from the solution and allowing it to dry. The solvent is usually selected so as to preferentially evaporate, leaving the active agent behind in the pores of the porous material.

This fairly simple process has been used to incorporate boron compounds (for example, boric acid) into wood for protection against borers. The wood to be treated is placed in an aqueous solution of the boron compounds until the solution has adequately soaked into the pores of the material. The process is fairly slow and depends on the nature of the wood and the cross-sectional area of the material which is to be impregnated. When the wood is believed to be sufficiently soaked through with the treating solution, it is removed from the bath and the solvent is allowed to drain off. The wood is then left to dry naturally before being used. The water content of such treated woods is usually very high when freshly treated.

In some cases alternate applications of vacuum and pressure are used to force the preservative solution into the wood. A vacuum may sometimes be used to remove excess fluid. However, the final drying step, in which the preservative binds to the wood, is invariably completed by natural drying because accelerated drying interferes with the binding process, degrades the product, or the capital equipment is too expensive for the time gained. This drying step is the rate determining step for the whole process.

One alternative impregnation process involves active ingredients dissolved in light organic solvents, usually referred to as LOSP (Light Organic Solvent Preservation) process. The LOSP process is widely used for the impregnation of wood with water-insoluble, organic active agents such as fungicides (for example copper naphthenate) and insecticides (such as synthetic pyrethroids).

The LOSP process has been used, for example, to incorporate copper naphthenate into radiata pine. Copper naphthenate is a fungicide available commercially as a 5% or 8% solution in liquid hydrocarbons. The copper naphthenate is diluted to a desired working strength by the addition of further quantities of hydrocarbon or white spirit, which act as a carrier. The radiata pine to be treated is placed in an autoclave which is flooded with the copper naphthenate solution. The timber is then subjected to various cycles that may involve vacuum or pressure, then the solvent is drained away and excess working solution is removed from the timber by vacuum. The treated timber is then removed from the autoclave, still wet with solvent. The residual solvent in the wood is typically left to evaporate naturally. Solvent remaining in the wood migrates to the wood surface by capillary action and eventually evaporates.

The LOSP process has a number of drawbacks. In particular, much of the solvent used is not recovered. In particular the solvent remaining in the wood after removal from the autoclave is lost to the atmosphere. The wood can also become difficult to handle and use if it is stacked in a manner which prevents complete solvent evaporation. This loss of solvent has a significant disadvantage from the points of view of cost and environmental impact. The solvents may also be hazardous, for example, be toxic, or flammable.

Further, the reliance on evaporation to remove excess solvent also means that the final drying step is slow. The result is a long entry-to-exit time of radiata pine at the treatment plant, or the release into use of incompletely dry product, leading to odour, painting and gluing problems. The delay in turnaround time to ensure adequate post-treatment drying has implications in terms of cost. Further, the LOSP process is also not amenable to the impregnation of wood with substances which have inherent low solubility in the solvent of choice. In order for wood to be retreated with an additional active agent, if this is necessary, the drying step needs to be wholly or substantially completed before the process can be repeated.

Alternative processes exist that involve contacting the wood with solvent vapours at elevated temperatures. Processes involving contacting hot solvent vapours with wood can result in the leaching of compounds, particularly fatty compounds, from the wood. This can be undesirable as the mechanical properties of the wood can be altered as a result of the leaching of compounds from the wood matrix by the hot solvent vapours.

A further alternative process uses aliphatic hydrocarbons such as propane, butane, pentane or mixtures thereof under pressure so that the aliphatic hydrocarbon is in the liquid phase as the carrier solvent. This now-discontinued Cellon (or, in Europe, Drilon) process used compressed liquid petroleum gas (LPG, typically propane and/or butane) with a co-solvent, under non-supercritical conditions, as carrier fluid for pentachlorophenol. A number of factors have been reported that tended to make the process uneconomical. These included the need to purge the treatment vessel with an inert gas before and after treatment to remove oxygen (to avoid creating explosive mixtures with the flammable LPG), the high insurance costs for such an operation, the energy required to recover the LPG (heating energy input, and long (1-3 hr) vacuum time required.

The replacement of LPG with non-flammable methylene chloride in the successor Dow process reduced the costs associated with purging and insurance, but the energy costs for recovery of this 40° C. boiling solvent were still too high. To the Applicant's knowledge, there is currently only one plant still operating with methylene chloride.

While the Cellon process has been abandoned, another process based upon a compressed gas carrier has been developed—using supercritical carbon dioxide.

A supercritical fluid is one that, under certain conditions, ceases to be a liquid and behaves like a gas, although retaining the solvent properties of a liquid. The supercritical fluid generally utilised in the wood treatment process is carbon dioxide, but other supercritical fluids can be utilised.

Carbon dioxide at a temperature greater than its critical temperature of 31.1° C. and a critical pressure of 72.9 atm. or 7.39 MPa is widely used as a supercritical fluid. This is mainly because supercritical carbon dioxide has a relatively low critical pressure and temperature, is readily available in large quantities, and is non-toxic, odourless, and non-flammable. Its surface tension becomes zero with a viscosity of about 320 pP (at 40° C. and 75.1 atm.). It is regarded as having very good solvent characteristics and is fairly environmentally sound without any exceptional pollution and waste disposal problems.

While supercritical $CO_2$ is the least expensive supercritical fluid, in absolute terms it remains extremely expensive. The first commercial supercritical $CO_2$ plant commenced operation in Hampen, Denmark in March 2002. The 60,000 $m^3 yr^{-1}$ plant required very heavy engineering to cope with a design operating pressure of 15,000 kPa with correspondingly high cost. Amortisation of such high capital costs imposes considerable strain on operational economic viability. Supercritical $CO_2$ techniques also have some other disadvantages associated with the extreme pressure changes. These can include collapse and distortion of the timber during treatment, and high variability in preservative retentions achieved. Accordingly, supercritical $CO_2$ technology is unlikely to replace methods and apparatus which rely on more traditional solvents in the near future for general use.

Supercritical $CO_2$ technology has however proved uniquely effective in treating refractory timbers, most particularly, spruce. Spruce is well known to be the "holy grail" of wood treatment and to date, it has only been treatable via the use of supercritical $CO_2$ techniques. Hydrofluoroalkanes or more generically, hydrofluorocarbons (HFCs), have not been widely used in impregnation methods due to their high cost, low solvency and significant greenhouse gas potential. Hydrofluoroalkanes, are commonly used in refrigeration applications, where they have largely superseded earlier refrigerants such as anhydrous ammonia, sulphur dioxide and Freon®. Chlorofluorocarbon (CFC) and hydrochlorofluorocarbon (HCFC) refrigerants marketed as Freon® were developed in the 1920s by DuPont to replace toxic inorganic gases, rapidly gaining adoption as they were odourless, colourless, nonflammable, and noncorrosive. In the 1990s, most uses of CFCs were phased out due to their damaging effect on the earth's ozone layer, and HCFCs became prominent for a few years because they are less damaging in this regard. However, the use of HCFCs is now generally being phased out, for example, in Australia by 2012. HFCs are the predominant class of refrigerant used worldwide today, as they do not harm the ozone layer at all, although they are acknowledged as powerful greenhouse gases, some having a global warming potential (GWP) thousands of times that of carbon dioxide. For this reason, HFCs are targeted under the Kyoto Protocol and are being replaced in many domestic refrigeration applications by straight hydrocarbons (HCs), such as propane. However, HFCs are still widely and lawfully available and used with appropriate precautions and regulations against discharge to the atmosphere for many applications where their properties are not matched by HCs.

Halocarbons are named industrially after the pattern HCFC-01234a where

0=number of double bonds in the molecule (omitted if zero),

1=number of carbon atoms −1 (omitted if zero),

2=number of hydrogen atoms +1,

3=number of fluorine atoms,

4=atom replaced by bromine ("B" prefix added), and a=a lower case suffix to distinguish isomeric forms.

The "normal" (unsuffixed) isomer is the most symmetrical and a, b, . . . are added as molecular symmetry decreases, or A=an upper case suffix to distinguish between commercialised mixtures of refrigerants.

Table 1 shows common halocarbons and other refrigerants and their relevant physical properties.

The present applicants have surprisingly found HFC's to be highly useful impregnation solvents, especially for refractive timbers.

It is an object of the present invention to overcome or ameliorate at least one of the disadvantages of the prior art, or to provide a useful alternative.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DESCRIPTION OF THE INVENTION

Figure 1:
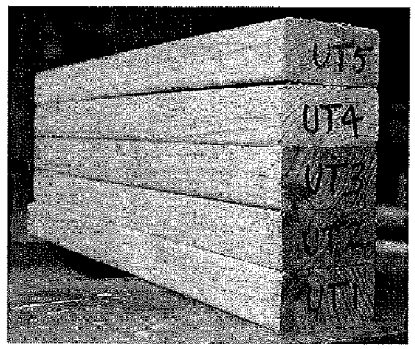
FIG. 1 is an end view of untreated specimens in accordance with the invention.

According to first aspect, the invention provides a non-supercritical method for impregnating a refractive timber substrate with an active agent, said method comprising:

a) preparing an impregnation fluid including a low boiling solvent and an active agent;

b) contacting a refractive timber substrate with said impregnation fluid in a liquid state in an impregnation chamber for a time sufficient to allow said fluid to penetrate the pores of said refractive timber substrate; and c) removing said impregnation fluid in a liquid state from said impregnation chamber and returning to a reservoir.

A refractory timber as used herein is used to refer to any timber species that has proven to be difficult to treat, in particular, with preservatives, biocides and the like. Timbers can usually be classified as "permeable" or "refractory". "Permeable" timbers are further classified as "permeable" or "somewhat permeable" timbers. Refractory timbers are further classified as (in decreasing order of permeability or penetrability) either "moderately refractory", "refractory" or "extremely refractory". "Refractory timber" as used herein refers to any moderately refractory, refractory or extremely refractory timber.

Refractory timbers include, but are not limited to:

Moderately Refractory:
Heartwood of radiata pine.

Refractory:
Spruce (*Picea*) species such as Norway spruce (*P. abies*) and sitka spruce (*P. sitchensis*); Douglas fir (*P. menziesii*), fir (*A. Alba*), poplar, willow, sapwood of cypress pine and certain eucalypt and pine species such as heartwood of messmate (*E. obliqua*).

Extremely Refractory:
Larch, western red cedar, European oak and American white oak.

Composite products can also be refractory or difficult to permeate, even when comprised of species not normally considered refractory. For example, plywood made from radiata pine sapwood can be very difficult to penetrate.

Preferably the method further comprises a subsequent step of entraining fluids in a gaseous state from said impregnation chamber, condensing said fluids to a liquid state and returning to said reservoir.

Preferably, the refractive timber substrate has no, or minimal, contact with solvent in the vapour phase.

Preferably, the impregnation fluid is removed from the treatment chamber and the treatment chamber is subject to vacuum to remove any residual low boiling fluid in the chamber.

Preferably, the impregnation fluid comprises as a solvent a low boiling hydrocarbon, low boiling hydrochlorofluorocarbon or hydrofluorocarbon.

The solvent may be selected from methane, ethane, propane, butane, isobutane, fluorinated hydrocarbons such as chlorodifluoromethane (R22), 1,1,1,2-tetrafluoroethane (R134a), 1,1,1-trifluoroethane (R143a), pentafluoroethane (R125), 1,1-difluoroethane (R152a) and difluoromethane (R32). Most preferably the solvent is pentafluoroethane (R125).

The impregnation fluid may also further comprise a co-solvent to solubilise the active in the low boiling solvent. Preferably the co-solvent is present in an amount of less than 5%. More preferably, it is present in an amount of less than 3%, even more preferably less than 2% and most preferably, present in an amount of less than 1%. As little as 1 ppb co-solvent may be used. The co-solvent preferably does not remain behind when the impregnation fluid is evaporated.

Preferably the co-solvent has a boiling point lower than the boiling point of the low boiling solvent. Most preferably the co-solvent forms an azeotrope or zeotrope with the low boiling solvent. If azeotropic mixtures are found, this allows the use of co-solvents which have a boiling point higher than that of the low boiling solvent. Preferably, the azeotropic mixture exists at the range of temperatures and pressures at which the low boiling solvent is volatilised. In one preferred embodiment, the co-solvent is trans-1,2-dichloroethylene.

A particularly preferred embodiment uses pentafluoroethane (R125) or a HFC as the low boiling solvent and trans-1,2-dichloroethylene as the co solvent. A particularly highly preferred embodiment involves the use of pentafluoroethane with trans-1,2-dichloroethylene, for example pentafluoroethane with 1-3% trans-1,2-dichloroethylene.

Preferably the impregnation fluid is removed from the treatment chamber in liquid form and the treatment chamber is subject to vacuum to remove any residual low boiling fluid in the chamber and/or from the refractory timber substrate Any suitable active may be used. In one embodiment, the active is a metallic biocide, such as a copper or tin naphthenate. Alternatively, the active may be a non-metallic biocide, such as an azole or pyrethroid, more particularly, propiconazole, tebuconazole or permethrin Impregnation may be repeated as necessary until a predetermined level of impregnation of the refractive timber substrate is achieved.

In another aspect, the invention provides a refractive timber substrate impregnated by a method of any one of the preceding claims.

Preferably, the invention provides a refractive timber substrate wherein the retention of active agent/refractive timber substrate is at least about 0.03% m/m in cross section, more preferably at least about 0.035% m/m in cross section or even more preferably at least about 0.04% m/m in cross section.

More preferably, the invention provides a refractive timber substrate wherein the retention of active agent/refractive timber substrate is at least about 0.02% m/m in the core region, more preferably at least about 0.025% m/m in the core region and most preferably at least about 0.03% m/m in the core region.

Preferably, the porous substrate for treatment is contacted by a liquid mixture of low boiling fluid containing active agent dissolved therein, with minimal or no contact of the material for treatment being contacted by low boiling solvent vapours. This may involve, for instance, flooding the treatment chamber from a lower portion of the treatment vessel, ie the treatment chamber is preferably flooded from an inlet at, near, or on the bottom, rather than the top. By keeping the material to be treated immersed in a liquid low boiling solvent/active, extensive ongoing leaching of substances from the material to be treated is controlled.

Preferably, the treatment vessel used to carry out the method of the present invention is sized and/or filled with porous material so as to be substantially full, i.e. with minimal volume occupied only by the liquid low boiling solvent/active mixture. The treatment vessel is therefore preferably sized with respect to the porous material intended to be treated, so the vessel is substantially filled with the porous material. Alternatively, the porous material is chosen in an amount and placed in the vessel such that the vessel is substantially full. In order to avoid large "dead volumes" of impregnation fluid, inert non-porous bodies can be placed in the chamber to fill voids.

The temperature and pressure are maintained in the treatment vessel such that the low boiling solvent/active are kept liquid at all times. If the mixture is allowed to become a vapour, either by reduction of amount of low boiling solvent/active or increase in temperature, the low boiling solvent may be vapourised but the less volatile active may not. In effect, a vapour phase depleted in terms of the amount of active will be generated which will become an extractive fluid, with the potential to remove any active already impregnated along with any other extractable components from the wood.

In a liquid low boiling solvent/active mixture, with a low dead volume, any native substances leached from the wood will soon equilibrate, and will not be extensively leached from the wood as may happen if contact was with the vapour phase.

Temperature can be controlled by heating or cooling, and pressure can be controlled by adding/removing an amount of the liquid low boiling solvent/active mixture from the treatment vessel.

Preferred temperatures of operation are in the range 40 to 60° C. Preferred pressures are in the range up to 2000 KPa.

Preferably the apparatus used to carry out the method of the present invention includes an entrainer maintained at a temperature similar to, or lower than that of the treatment vessel, with any liquid or vapour being drawn from the treatment vessel under low pressure. Desirably residual heat contained in the timber provides a heat source for the evaporation of the liquid contained in the timber whilst the entrainer maintains a controlled temperature and pressure to extract the vapours.

Desirably, heat exchangers operate with the entrainer to provide a heat balance and to control pressure differentials throughout the system. One heat exchanger operates to warm the impregnation fluid in the first fluid pathway and increase the pressure thereof prior to entering the treatment vessel. Another heat exchanger may operate to cool the residual impregnation fluid and provide a low pressure at the entrainer to further cool and condense the mixture. The pressures and temperatures are related by the vapour pressure/temperature properties of the selected solvent but may be modified with respect to the pressure/temperature characteristics of the pure substance by the presence of the active agent or agents. The use of the entrainer minimises solvent losses and aids in solvent recycling.

Most preferably, the apparatus used to carry out the method of the present invention is a closed system which allows for recovery and recycling of the solvent, and where the system is adapted to be fluid tight at elevated pressures.

It is preferred if the system can be evacuated to remove air prior to commencement of the process, and can allow reintroduction of air to atmospheric pressure in a controlled manner when the process is completed.

Preferably, the porous substrate has no, or minimal, contact with solvent in the vapour phase.

Once the impregnation fluid has been removed from the treatment chamber, the treatment chamber may be subject to vacuum to remove any residual low boiling fluid in the chamber and/or in the porous substrate.

Preferably, the impregnation fluid is prepared by direct introduction of said active agent into said solvent.

Preferably, the active mixture is introduced into the treatment vessel at a controlled rate and at a predetermined temperature. Suitable temperatures and pressures are selected depending on the nature of the solvent used and the soluble substances desired to be impregnated as well as the size and porosity of the substrate.

Preferably, the method of the present invention is operated in a continuous fashion. In one highly preferred method of operation, the steps may be repeated continuously until the desired levels of impregnation of the substrate have been reached.

The invention is not restricted to any particular active. Any active soluble in the low boiling solvent, or soluble in the low boiling solvent/co-solvent mixture may be used.

It is preferred if the active is biocidal. Any suitable metallic biocides such as copper or tin naphthenates, or non-metallic biocides such as azoles or pyrethroids, may be used in the apparatus and process of the present invention. Other suitable actives include creosote (including coal tars) CRT, pentachlorophenol and related chlorophenols PCP, disodium octaborate tetrahydrate BOC, copper-8-quinolinolate CUQ and zinc naphthenate.

However, non biocidal actives, such as pigments, dyes, perfumes, sealants etc are all contemplated as being impregnated into porous materials. While this invention is described with reference to wood as the porous material, it will be understood that any porous material, natural or man-made, organic or inorganic, may be impregnated by the apparatus and method disclosed herein.

In other embodiments of the invention, it is possible to carry out multiple impregnation steps—for example, with multiple biocides. It is also possible to carry out multiple sequential impregnation steps, where different penetration levels of different agents are desired. For example, in one preferred embodiment, wood could be treated with a biocidal agent in a manner to achieve full penetration. Subsequent to this, a partial or envelope penetration with a water repellent treatment and/or a colouring agent could be used.

The apparatus of the present invention can employ single or multiple reservoirs or inlet ports to facilitate multiple impregnation steps.

According to another aspect, the invention provides a refractive timber substrate impregnated according to the method of the present invention.

A co solvent, if used, can be added either to the treatment agent immediately prior to entering the fluid pathway or it can be premixed in a reservoir. Alternatively, co-solvent may be dosed in at an appropriate point. Preferably, co-solvent and treating agent are combined in a reservoir prior to use.

Discussion with reference to a low boiling solvent herein is taken to include reference to a single low boiling solvent, a mixture of low boiling solvents and or any co-solvents as required.

The impregnation fluid, comprising low boiling solvent and active is brought into contact, in a liquid state, with the refractory porous substrate in a treatment vessel. Following treatment with the liquid impregnation fluid for the desired time, the liquid impregnation fluid is removed. It may be treated further, for example allowed to expand, causing the active agent to drop out of solution for reuse, or the whole impregnation fluid may be returned to a reservoir for re-use.

The porous substrate, impregnated with impregnation fluid, may then be subjected to vacuum, to remove the low boiling solvent and co solvent and leave the substrate impregnated with the treatment agent. The low boiling solvent and co solvent may be condensed and returned to a reservoir for further use.

A source of low boiling solvent at a predetermined temperature and pressure initially supplies the liquid solvent to a fluid junction where it admixes with an active agent. Co-solvent is added to the active at an appropriate point prior to introduction into the treatment chamber if required. The active solution thus produced (the impregnation fluid) is then passed to a treatment vessel at a predetermined temperature and pressure. The treatment vessel contains a porous substrate, such as portions of wood to be treated. The porous substrate is maintained in contact with the solvent active mixture for a desired period of time, usually a few minutes. The solvent and active agent migrate into the pores. Without wishing to be limited by theory it is believed that there is no preferential uptake of active over solvent or vice versa. What is preferential is the subsequent preferential removal of low boiling solvent over active agent. The liquid material in the treatment chamber is pumped off until only a saturated vapour remains. Overall, there is a drop in pressure in the treatment chamber allowing the agent to remain in the porous material while removing low boiling solvent molecules.

The wood is at a slightly higher temperature than the surroundings as it retains some sensible heat from the compressed gas. The atmosphere in the treatment chamber, which may be a gas or saturated vapour contains the solvent and co solvent plus any volatile portion of unused active agent not taken up into the porous material, is then removed from the treatment vessel by an entrainer. In the entrainer the gases and liquids and any excess active agent are further condensed for re use. Further active agent and co solvent may be added at if required. In an alternative embodiment, a plurality of treatment vessels may be used to cycle through a range of batch processes. Porous substrate can be loaded into one vessel, while impregnation is taking place in one or more other vessels.

A number of prior art impregnation procedures have required the use of antiblooming agents when impregnating porous substrates. These antiblooming agents, such as for example, glycols, are required to prevent a "bloom" of active agent from forming on the surface of the porous substrate as the solvent is removed.

The use of the method of the present invention does not require the addition of antiblooming agents. The present invention enables the low boiling solvent to be removed from the porous substrate without the formation of blooms of an active agent on the surface. Preferably, the method of the present invention uses an impregnation fluid which does not contain an antiblooming agent.

It may be possible to increase the load of active agent in a low boiling solvent by the use of a co-solvent. It is important that the co-solvent be compatible with the low boiling solvent. It is further important that the co-solvent not remain as a residue in the wood once the low boiling solvent is evaporated. The co-solvent should therefore be either itself be extremely low boiling, or form an azeotrope or zeotrope with the low boiling solvent.

A particularly suitable blend has been serendipitously found by the present applicants to be a combination of pentafluoroethane as low boiling solvent and trans-1,2-dichloroethylene as co solvent. The trans-1,2-dichloroethylene is preferably present in amounts of less than 5%, more preferably less than 3%. Despite the fact that trans 1,2-dichloroethane boils at about 48° C., and pentafluorethane boils at −48.5° C., small amounts of the former form an azeotropic or zeotropic mixture with the latter. Experimentally, solutions of 1%, 2% and 3% of trans-1,2-dichloroethylene in pentafluoroethane were found to evaporate fully at 25° C., leaving no residue of trans-1,2-dichloroethylene.

Monitoring of uptake of actives can be performed by analysis of the reservoir material by HPLC, GC, GC/MS and the like, or by simply determining the weight of active residue in an aliquot of the impregnation fluid. Being a closed system, any component of the mixture depleted from the active mixture must be incorporated into the substrate for impregnation. In this way, the uptake of additives can be carefully monitored, as well as the depletion of any solvent additives (for example, flash point suppressants).

If desired, the impregnation processes can be repeated many times. In this way, the amount of active can be accumulated into the porous substrate to an extent not normally achievable by simply soaking. Any given solvent will be able to dissolve a maximum load of active. When the solvent is evaporated, the wood will have deposited active present in the pores. This will not prevent a further charge of fully laden solvent from carrying further active into the wood because none of the previously deposited active will, in fact, be able to re-dissolve into the saturated solvent. When the solvent is removed, further active is accumulated into the wood. The process can be repeated, topping the active up in the solvent if desired.

Alternatively, it may be possible just to treat the porous substrate with a single application of active.

Surprisingly, HFCs have been found to be useful for impregnation of refractory timbers at subcritical pressures; in fact, some require no higher pressure than a conventional waterborne treatment process, generally viewed as being about 1380 kPa (200 psi). Other HFCs may require somewhat higher operating pressure, particularly if desired to operate at higher temperature, but still far less than pressures required for supercritical carbon dioxide.

HFC's do not share the most significant disadvantages of currently used carriers. At 'conventional' operating pressures, they are capable of rapid, full penetration of some timbers generally considered refractory, such as spruce and the heartwood of radiata pine HFCs are typically non-flammable, and their non-polar (non-swelling) characteristics suggest potential suitability as replacements for current non-swelling solvents such as white spirits used in light organic solvent preservative (LOSP) treatments of timber in final form. Non-flammability provides operational safety advantages over current LOSP solvents and their much lower boiling points offer greatly improved prospects for economically viable solvent recovery after treatment. Full recovery of the carrier fluid would eliminate current concerns with LOSP treatments on atmospheric pollution grounds

EXAMPLES

Refrigerants were typical technical refrigerant grades purchased from normal commercial sources. The co-solvent trans-1,2-dichloroethylene (TDCE) where used was of technical grade. Active biocide ingredients in technical form (unformulated, generally 95-98% purity) were obtained from manufacturers.

Solubility tests were performed in pressure-rated glass tubes. Required amounts of active ingredient (and co-solvent where required) were weighed into the tubes before sealing. The appropriate quantity of pressurised refrigerant was injected into the tube and the temperature was adjusted to the target. Solubility was determined by visual inspection after agitation at the target temperature.

Timber was 70 mm×35 mm kiln-dried softwood framing material; radiata pine (*Pinus radiata* D. Don) MGP10 grade under Australian Standard AS/NZS1748:2006 (Standards Australia 2006) was supplied from Australian plantations by Carter Holt Harvey; Norway spruce (*Picea abies* H. Karst.) was supplied from European sources by Moxon Timbers, an Australian importer. Timber was docked into 500 mm or 1000 mm length specimens and end-sealed with an impervious cross-linking epoxy resin prior to treatment.

The methodology used was in accordance with that disclosed in our copending application, published as WO2006/092673, the contents of which are incorporated herein by reference.

Treatments were applied in inexpensive steel impregnation vessels capable of containing an appropriate number (5 or 30) of 70×35 mm timber specimens together with the necessary fluid to maintain coverage during the treatment process. Attached equipment included necessary vacuum, pressure and transfer pumps, heat exchangers and jackets, low-boiling fluid storage reservoirs, transfer lines and mixing junctions or vessels. Treatments included a variety of combinations of timber species, low-boiling carrier fluid, co-solvent, active ingredients, contact time, temperatures and pressures.

Where a co-solvent was used, the active ingredients were first dissolved in the total required amount of co-solvent and drawn into an evacuated mixing vessel. The required amount of pressurised refrigerant was then pumped into the mixing vessel for mixing and any pre-heating required. When the desired operating temperature was reached, the preservative fluid was transferred to the evacuated impregnation vessel containing the timber and maintained at the target temperature for the target contact time. On completion, excess fluid was pumped back to the storage reservoir before applying a recovery vacuum to the impregnation vessel. Evacuated, recovered refrigerant and co-solvent from the vacuum pump were re-condensed and combined with the bulk fluid in the storage reservoir.

Any net usage of carrier fluid was assessed by weighing the fluid in the storage reservoir together with any added co-solvent before and after the charge. Solutions of active ingredients in carrier fluid were sampled under pressure before and after the charge. Weight losses were monitored as refrigerant and any co-solvent were removed sequentially from the fluid sample by carefully controlled evaporation. Remaining active ingredients in the non-volatile residue were dissolved in an appropriate chromatography-grade organic solvent and analysed using gas chromatography against analytical grade standards for the biocides used.

Dimensional changes due to treatment were monitored by measuring width and thickness at three points along the length of specimens before and after treatment, using digital callipers reading to 0.01 mm.

Analytical samples were cut from the mid-length region of each treated timber specimen to determine compliance with retention and penetration requirements of Australian Standard AS1604.1-2005 (Standards Australia 2005) for H3 (above ground weather exposed) end use situations. For timber specimens containing predominantly sapwood, cross-section and core (the central one-ninth of the cross-section) zones were taken for analysis. For timber specimens containing predominantly heartwood, or for spruce, the outer 5 mm and core zones were taken. In each case, in the absence of a visual penetration test, the core sample was analysed to determine whether full penetration had occurred. The sapwood cross-section sample was analysed to determine retention of preservative components, as this is the zone for which a minimum preservative retention is specified in the Standard. With regard to heartwood, only the outer 5 mm zone is required to be penetrated under the Standard, so this zone was also analysed to confirm penetration.

Each analytical sample was ground and extracted, and extracts were analysed for active ingredients using gas chromatography with either electron capture or nitrogen-phosphorus specific detector, using methods specified in the Australian Standard AS1605.3-2006 (Standards Australia, 2006).

Solubility of Active Ingredients

The HCFC R-22 has sufficient solvency to carry a wide range of organic timber preservatives without the use of co-solvents. This is even true for the active ingredients of lower specific efficacy, such as copper- and tri-n-butyl tin naphthenate (CuNap, TBTN). Early experiments were conducted in R-22 containing 3% of a CuNap concentrate containing 8% Cu, without experiencing any need to add a co-solvent. Subsequent work was conducted using 1% TBTN and 0.2% permethrin in R-22 alone, again without co-solvent. The use of these organometallic active ingredients, for which rapid colorimetric penetration tests are available, simplified the early work exploring minimum schedules to achieve required depths of penetration of various timber species. However, HFCs lack comparable native solvency for both the organometallics and some newer organic active ingredients of higher specific activity, such as tebuconazole. Maximum practical solubilities of active ingredients of current interest in a typical refrigerant—co-solvent pair (R-125±co-solvent over 20°-60° C. range) are given in Table 2.

A few percent of a co-solvent are typically required to dissolve the triazole ingredients (particularly tebuconazole) at the concentrations necessary to achieve target retentions in the treated product in a single treatment step.

Penetration and Retention in Timber

Table 3 gives the results of chemical analysis of a test charge of radiata pine specimens treated at 40° C. and 1930 kPa pressure for a contact time of 30 minutes with a solution of 3% TDCE, 0.12% propiconazole, 0.06% tebuconazole, 0.04% permethrin and 0.03% IPBC in R-125. There were ten specimens consisting predominantly of heartwood, and eleven of sapwood. Mean wood density was 480 kg·m$^{-3}$.

All sapwood specimens and 8 of 10 heartwood specimens met H3 retention and penetration requirements of the Standard. Retention gradients in the sapwood were excellent-core retentions averaged 85-90% of cross-section retentions. The 5 mm heartwood penetration requirement was far exceeded, with all heartwood specimens fully penetrated by all actives. Two heartwood specimens did not contain the required minimum amount of permethrin in the outer 5 mm zone. Some wood resin was observed on the surfaces of these specimens, evidently mobilised and relocated during treatment. It is considered most unlikely that the commonly-used LOSP treatment process would have achieved the required 5 mm zone retention in these resinous specimens.

Table 4 gives the results of chemical analysis of a test charge of eight spruce specimens treated at 40° C. and 1930 kPa pressure for a contact time of 30 minutes with a solution of 3% TDCE, 0.12% propiconazole, 0.06% tebuconazole, 0.04% permethrin and 0.03% IPBC in R-125. Mean wood density was again 480 kg·m$^{-3}$. As it is difficult to distinguish between heartwood and sapwood in this species, all specimens were analysed in three zones, covering both possibilities.

In the absence of effective tests to distinguish heartwood from sapwood, it is not possible to readily assess compliance with the Australian Standard. However, if we consider the material as heartwood because of its characteristic impermeability, all specimens met H3 penetration requirements of the Standard. All specimens were fully penetrated, with evidence of active ingredient present in the core in all specimens. In one specimen only, while the core zone contained measurable amounts of each triazole (0.004%, 0.005%), that zone contained less than the detection limit of 0.001% permethrin. Retention gradients were steeper than those obtained in radiata pine using the same conditions. Core retentions averaged 29-48% of cross-section, compared to 85-90% in radiata pine sapwood—but these were much greater than expected for this species, which would not generally be expected to be penetrated at all in the core zone. The outer 5 mm zones were quite well treated, averaging much more than the retentions required by the Standard, although four of the specimens contained 10-30% less than that required. This could be remedied by simply increasing the concentration of active ingredients in the treatment fluid. Conventional wood preservation solvents (water or light organic solvents) do not produce anything like this outcome in spruce, with the possible exception of a supercritical carbon dioxide process.

Table 5 gives the results of chemical analysis of a test charge of five radiata pine specimens treated at 40° C. and 2100–2340 kPa pressure for 30 minutes with a solution of 3% TDCE, 0.057% propiconazole, 0.033% tebuconazole and 0.053% permethrin in R-410A. Mean wood density was 536 kg·m$^{-3}$. All five specimens consisted of 100% sapwood. All specimens were analysed in four zones, viz, full cross-section, core (inner one ninth of the cross-section), outer 5 mm zone, and the intermediate zone between outer and core zones.

All specimens met H3 retention and penetration requirements of the Standard. Retention gradients in the sapwood were again excellent-core retentions averaged 85-95% of cross-section, with very low co-efficents of variation.

Table 6 gives the results of chemical analysis of a test charge of five radiata pine specimens treated at 70° C. and 1960–2020 kPa pressure for 30 minutes with a solution of 3% TDCE, 0.033% propiconazole, 0.033% tebuconazole and 0.022% permethrin in R-134a. Mean wood density was 464 kg·m$^{-3}$. Three specimens consisted of 100% sapwood, while the other two had more than 50% heartwood. Sapwood specimens were analysed in two zones, viz, full cross-section and core (inner one ninth of the cross-section). Heartwood-containing specimens were analysed in four zones, viz, cross-section of the sapwood, cross-section of the heartwood, heartwood core (inner one ninth of the cross-section of the heartwood), and the outer 5 mm zone of the heartwood.

All specimens met the penetration requirements of the Standard. Even at these reduced concentrations of active ingredient in the treatment fluid, sapwood cross sections met H3 retention requirements, but the heartwood outer zones contained slightly less permethrin than required. This was clearly due, at least in part, to heavy resinosis of the heartwood in these specimens, which exhibited visible translocated resin on surfaces after treatment. One of the heartwood core samples was so resinous that state-of-the-art capillary gas chromatography could not resolve the permethrin isomer peaks from interfering resin peaks, so that no analytical result could be reported for that sample. The slightly deficient outer heartwood zone permethrin retentions could be rectified by a slight increase in treatment fluid concentration. Retention gradients in the sapwood were again excellent—mean core retentions of the triazole fungicide components actually slightly exceeded the corresponding mean cross-section retentions. Such flat preservative concentration gradients would contribute to excellent economies of treatment, avoiding the need to over-treat surface zones in order to achieve specified core or cross-sectional retentions.

The results obtained by the methods of the present invention are very favourable in comparison with the results obtained from treating refractory timbers with other solvents.
Dimensional Stability of Treated Timber Radiata pine specimens for which penetration and retention data is given in Table 5 were evaluated for dimensional stability during this relatively intensive (70° C., 2000 kPa) process. Dimensions of specimen width (generally tangential direction) and thickness (generally radial) are compared with dimensions of untreated equivalent material in Table 7.

There was a slight increase in dimensions and dimensional variability due to the treatment.

Figure 2:
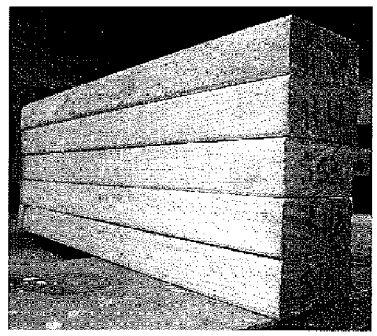
FIG. 2 is an end view of treated specimens in accordance with the invention.
Figure 3:
FIG. 3 is a face view of untreated specimens in accordance with the invention.
Figure 4:
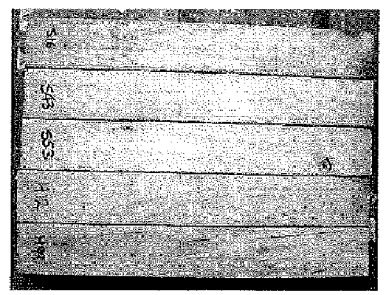
FIG. 4 is a face view of treated specimens in accordance with the invention.

FIGS. 1 to 4 illustrate the condition of the specimens before and after treatment. The treatment process caused no discernable distortion.

Surprisingly, the present inventor has found that hydrofluoroalkanes offer opportunities as carrier fluids for treating timber in its final shape and form for above-ground end use situations. HFC-based processes have a number of advantages over alternate treatment systems intended for these products including minimal dimensional change or distortion of the treated product, operating pressures that will not require extremely expensive plant, much lower boiling points than solvents currently used in LOSP systems with correspondingly better efficiencies for solvent recovery, and remarkable abilities to penetrate refractory timber.

REFERENCES

Australian Standard AS 1604.1 (2005): *Specification for preservative treatment. Part 1: Sawn and round timber*. Standards Australia, Sydney, New South Wales, Australian/New Zealand Standard AS/NZS 1605.3 (2006): *Methods for Sampling and Analysing Timber Preservatives and Preservative-Treated Timber.—Part 3—Analysis methods for determination of preservative retention*, Standards Australia and Standards New Zealand, Sydney, New South Wales.

Australian/New Zealand Standard AS/NZS 1748 (2006): *Timber—Mechanically stress-graded for structural purposes* Standards Australia and Standards New Zealand, Sydney, New South Wales.

The invention claimed is:

1. A non-supercritical method for impregnating a refractive timber substrate with an active agent, said method including:
   a) preparing an impregnation fluid including a low boiling solvent and an active agent;
   b) contacting a refractive timber substrate with said impregnation fluid in a liquid state in an impregnation chamber for a time sufficient to allow said fluid to penetrate the pores of said refractive timber substrate; and
   c) removing said impregnation fluid in a liquid state from said impregnation chamber and returning to a reservoir; and wherein the refractory timber is selected from the group consisting of heartwood of radiata pine, Spruce (*Picea*) species, Douglas fir (*P. menziesii*), fir (*A. Alba*), poplar, willow, sapwood of cypress pine, eucalypt species, pine species, larch, western red cedar, European oak and American white oak.

2. A method according to claim 1 including a subsequent step of entraining fluids in a gaseous state from said impregnation chamber, condensing said fluids to a liquid state and returning to said reservoir.

3. A method according to claim 1 wherein the refractive timber substrate has no, or minimal, contact with solvent in the vapour phase.

4. A method according to claim 1 wherein the impregnation fluid is removed from the treatment chamber and the treatment chamber is subject to vacuum to remove any residual low boiling fluid in the chamber.

5. A method according to claim 1 wherein the impregnation fluid comprises as a solvent a low boiling hydrocarbon, low boiling hydrochlorofluorocarbon or hydrofluorocarbon.

6. A method according to claim 1 wherein the solvent is selected from the group consisting of methane, ethane, propane, butane, isobutane, and fluorinated hydrocarbons.

7. A method according to claim 1 wherein the solvent is pentafluoroethane (R125).

8. A method according to claim 1 wherein the impregnating fluid further includes a co-solvent to solubilise the active in the low boiling solvent.

9. A method according to claim 8 wherein the co-solvent is present in an amount of less than 5%.

10. A method according to claim 8 wherein the co solvent has a boiling point lower than the boiling point of the low boiling solvent.

11. A method according to claim 9 wherein the co solvent forms an azeotrope or zeotrope with the low boiling solvent.

12. A method according to claim 9 wherein the co solvent is trans-1,2-dichloroethylene.

13. A method according to claim 9 wherein the low boiling solvent is pentafluoroethane (R125) or a HFC and the co solvent is trans-1,2-dichloroethylene.

14. A method according to claim 1 wherein the impregnation fluid is removed from the treatment chamber and the treatment chamber is subject to vacuum to remove any residual low boiling fluid in the chamber and/or from the refractory timber substrate.

15. A method according to claim 1 wherein the active is a metallic biocide, such as a copper or tin naphthenate.

16. A method according to claim 1 wherein the active is a non-metallic biocide, such as an azole or pyrethroid.

17. A method according to claim 16 wherein the active is propiconazole, tebuconazole or permethrin.

18. A method according to claim 1 wherein impregnation is repeated until a predetermined level of impregnation of the refractive timber substrate is achieved.

19. A method according to claim 1 wherein the refractory timber is spruce (*P. abies*).

20. A method according to claim 1 wherein the refractory timber is radiata pine (*P. radiata*) heartwood.

21. A method according to claim 1 wherein the refractory timber is messmate (*Eucalyptus obliqua*) heartwood.

22. A refractive timber substrate impregnated by a method of claim 1.

23. A refractive timber substrate according to claim 22 wherein the retention of active agent/refractive timber substrate is at least about 0.03% m/m in cross section.

24. A refractive timber substrate according to claim 22 wherein the retention of active agent/refractive timber substrate is at least about 0.02% m/m in the core region.

25. A method according to claim 1 wherein the Spruce (*Picea*) species is Norway spruce (*P. abies*) or sitka spruce (*P. sitchensis*).

26. A method according to claim 6 wherein the fluorinated hydrocarbon is selected from the group consisting of chlorodifluoromethane (R22), 1,1,1,2-tetrafluoroethane (R134a), 1,1,1-trifluoroethane (R143a), pentafluoroethane (R125), 1,1-difluoroethane (R152a) and difluoromethane (R32).

27. A refractive timber substrate according to claim 22 wherein the retention of active agent/refractive timber substrate is at least about 0.025% m/m in cross section.

28. A refractive timber substrate according to claim 22 wherein the retention of active agent/refractive timber substrate is at least about 0.035% m/m in cross section.

29. A refractive timber substrate according to claim 22 wherein the retention of active agent/refractive timber substrate is at least about 0.04% m/m in cross section.

* * * * *